US005554129A

United States Patent [19]
Stevenson

[11] Patent Number: 5,554,129
[45] Date of Patent: Sep. 10, 1996

[54] SAFETY CAP AND HUB FOR MEDICAL INSTRUMENTS

[76] Inventor: John A. Stevenson, 14835 Telegraph Rd., Santa Paula, Calif. 93060

[21] Appl. No.: 345,611

[22] Filed: Nov. 28, 1994

[51] Int. Cl.⁶ ..................................................... A61M 5/32
[52] U.S. Cl. ........................ 604/192; 604/110; 604/263
[58] Field of Search .................................. 604/192, 110, 604/181, 187, 197, 199, 198, 263, 272

[56] References Cited

U.S. PATENT DOCUMENTS

| | | |
|---|---|---|
| 3,559,645 | 2/1971 | Schaller. |
| 4,240,427 | 12/1980 | Akhavi. |
| 4,468,223 | 8/1984 | Minagawa. |
| 4,846,811 | 7/1989 | Vanderhoof. |
| 4,874,384 | 10/1989 | Nunez. |
| 4,883,470 | 11/1989 | Haindl. |
| 4,986,817 | 1/1991 | Code ..................................... 604/192 |
| 5,026,345 | 6/1991 | Teringo .............................. 604/263 X |
| 5,053,018 | 10/1991 | Talonn. |
| 5,176,633 | 1/1993 | Sit. |
| 5,342,309 | 8/1994 | Hausser. |

FOREIGN PATENT DOCUMENTS

W09206724  4/1992  Germany.

*Primary Examiner*—Corrine M. McDermott
*Assistant Examiner*—N. Kent Gring
*Attorney, Agent, or Firm*—Koppel & Jacobs

[57] ABSTRACT

A free-standing safety cap includes a first compartment for temporarily securing an unused medical instrument and a second compartment for permanently securing a used medical instrument. The instruments have a sharp end, and are fitted with a hub. The first compartment has an opening through which the unused instrument can be removed. A stand supports the cap in a position in which an opening in the second compartment is exposed to receive the used instrument without the user having to hold the cap. A locking mechanism, preferably one-way, is provided for engaging the hub and permanently securing the sharp end of the used instrument inside the second compartment.

18 Claims, 6 Drawing Sheets

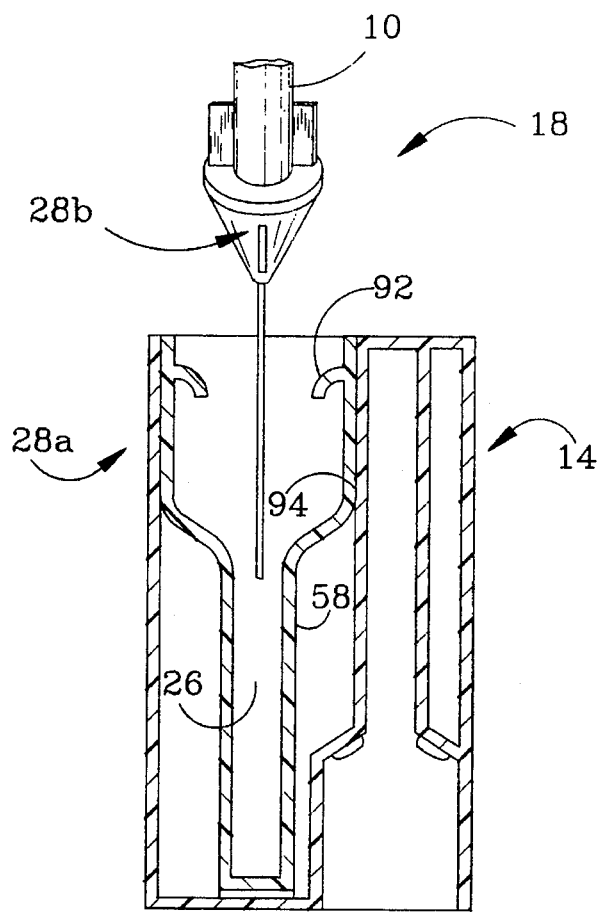
FIG.8
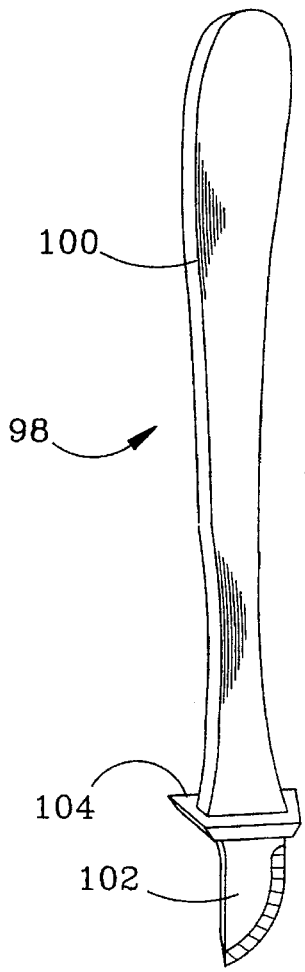
FIG.9
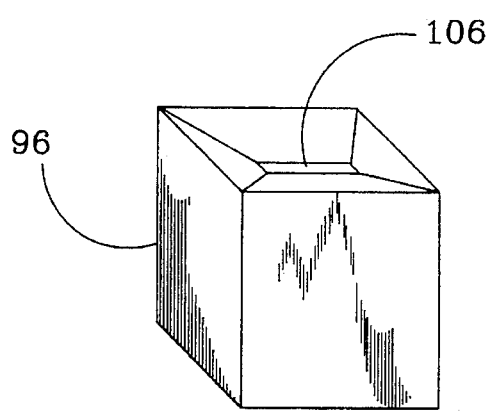

SAFETY CAP AND HUB FOR MEDICAL INSTRUMENTS

BACKGROUND OF THE INVENTION

1. Field of the Invention

The present invention generally relates to the storage and disposal of sharp medical instruments such as contaminated hypodermic needles, and more specifically to a safety cap and instrument hub.

2. Description of the Related Art

Hypodermic needles are used to give injections and draw blood from patients. These needles can become contaminated with any number of infectious and potentially lethal diseases. Other medical instruments such as scalpels can become similarly contaminated. The threat of accidental puncture wounds from contaminated needles or scalpels poses a significant safety risk to medical personnel, hospital cleaning staff, waste disposal workers and the general public.

Until the early 1980's, it was standard practice to "recap" a needle after use. This required the user to grasp the narrow plastic sleeve in one hand, and with the other hand insert the contaminated needle into the sleeve. These sleeves were designed primarily to provide physical protection for the needle and to maintain sterility before use. Because of the sleeve's size and shape, a user could very easily miss the sleeve and puncture his or her hand. Furthermore, the cap could be accidentally or intentionally removed, thereby exposing the contaminated needle.

The medical community recognized this danger and adopted a policy against recapping. Instead, medical treatment areas are supposed to be equipped with special "sharps containers" for disposing contaminated sharp objects such as hypodermic needles or scalpels. These containers are typically fitted with either flexible plastic flaps or fixed baffles over their openings. The flaps are formed from a plastic diaphragm which has a hole at its center with slits extending radially outward from the hole. These designs are supposed to allow contaminated objects to be pushed through the opening, but prevent them from falling back out of the container. As a practical matter, sharps containers cannot be provided immediately adjacent every location where injections are being given, blood is being drawn or incisions are being made. Therefore, the user must carry the exposed contaminated needle or scalpel some distance before disposing of it. Furthermore, the sharp instruments have managed to back out of the container's opening or poke through its walls, posing a significant safety risk.

U.S. Pat. No. 4,883,470, "Safety Cap", discloses a flared cap for storing the needle and cannula hub before and after use. The cap and cannula hub have complementary rib designs which allow a syringe to both engage the hub and remove the needle from the cap prior to use, and to reinsert the contaminated needle into the cap and disengage the syringe. The flared cap reduces the risk of self-puncture, but the user must still grasp the cap with his off hand to recap the needle. Furthermore, the recapped contaminated needle can be withdrawn from the cap by reengaging a syringe.

U.S. Pat. Nos. 4,846,811, 4,874,384, 5,342,309 and 5,053,018 disclose slidable or telescoping sleeves that fit over the syringe. The sleeves are retracted to expose the needle, and then slid down and locked to shield the tip. These syringes are awkward to use due to the extra bulk on the syringe itself. Furthermore, the incorporation of moveable parts increases the cost and reduces the reliability; moving parts break.

SUMMARY OF THE INVENTION

The present invention seeks to provide a simple and cost effective safety cap and instrument hub that allow the user to permanently store a contaminated instrument in the safety cap without having to grasp the cap to reinsert the used instrument.

This is accomplished with a free-standing safety cap that includes a first compartment for temporarily securing an unused medical instrument, and a second compartment for permanently securing a used instrument. The medical instrument has a sharp end, and is fitted with a hub. The first compartment has an opening through which the instrument can be removed. A stand supports the cap in a position in which an opening in the second compartment is exposed to receive the used instrument. A locking mechanism, preferably one-way, is provided for engaging the instrument's hub and permanently securing the sharp end of the instrument inside the second compartment.

For a better understanding of the invention, and to show how the same may be carried into effect, reference will now be made, by way of example, to the accompanying drawings.

BRIEF DESCRIPTION OF THE DRAWINGS

FIG. 8 is a sectional view of an alternative embodiment of the safety cap and hub; and FIG. 9 is a prospective view of an alternative embodiment of a safety cap and scalpel.

DETAILED DESCRIPTION OF THE INVENTION

The invention provides a safety cap and instrument hub design that reduce the risk of accidental puncture wounds for contaminated medical instruments such as hypodermic needles and scalpels. The user places the cap on a flat surface and reinserts the contaminated instrument. The cap allows the user to permanently secure the used instrument without having to grasp the cap in his or her off hand. Furthermore, the cap and hub preferably provide a one-way locking mechanism that permanently secures the sharp end of the contaminated instrument inside the cap. This greatly reduces the risk of accidental puncture wounds to the cleaning and waste disposal personnel. The safety cap and instrument hub are described with respect to a hypodermic needle-hub assembly but are applicable to other types of sharp medical instruments.

Figure 1:
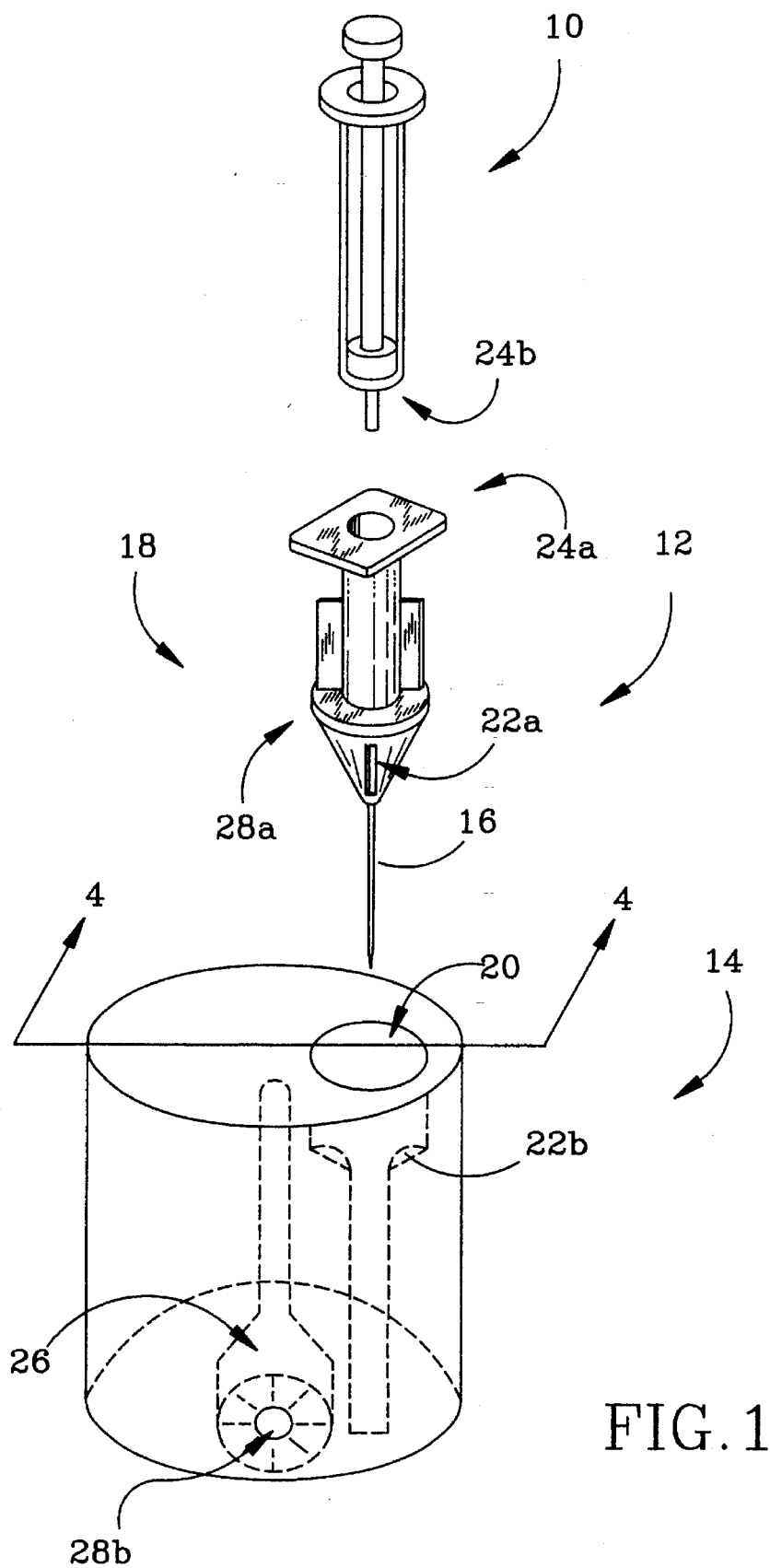
FIG. 1 is a partially exploded view of a syringe, hypodermic needle-hub assembly and safety cap.

FIG. 1 is a partially exploded view of a syringe 10, a hypodermic needle-hub assembly 12 and a safety cap 14. The hypodermic assembly includes a needle 16 and a hub 18. The sterilized hypodermic assembly is secured in a compartment 20 in the cap. The hub and cap are provided with complementary locking mechanisms 22a and 22b, respectively, for temporarily securing the cap in compartment 20. The cap 14 and hypodermic assembly 12 are sealed in a protective package (not shown) and sterilized. The syringe may be packaged separately or together with the cap and hypodermic assembly. In some cases the syringe and hypodermic assembly are formed as an integral unit.

To give an injection or draw blood, the user breaks the seal, attaches the syringe to the assembly 12 and removes it from the safety cap 14. The hub and syringe are formed with complementary couplings 24a and 24b, respectively, for coupling the needle to the syringe so that fluid can pass from the syringe to the needle and vice versa. The standard coupling mechanism is a luer-lock flange, although other coupling mechanisms can be used.

Once the needle has been contaminated, the user flips the cap over, places it on a flat surface such as a table or counter top, and inserts the used hypodermic into a compartment 26. To reduce the size of the safety cap, the compartments 20 and 26 are preferably formed in opposite ends of the cap. Once the needle has been safely confined inside the compartment 26, the user may disengage the syringe and dispose of the cap and syringe, or may dispose of the cap with the syringe engaged.

The hypodermic assembly 12 and safety cap 14 are provided with complementary locking mechanisms 28a and 28b, respectively, for permanently securing the assembly 12 inside the compartment 26 and disengaging the syringe. The locking mechanisms preferably form a one-way lock; once the contaminated needle is inserted into the compartment 26, it cannot be removed. The invention is described with respect to a push-through type locking mechanism, but could use a number of different locking configurations.

Figure 2:
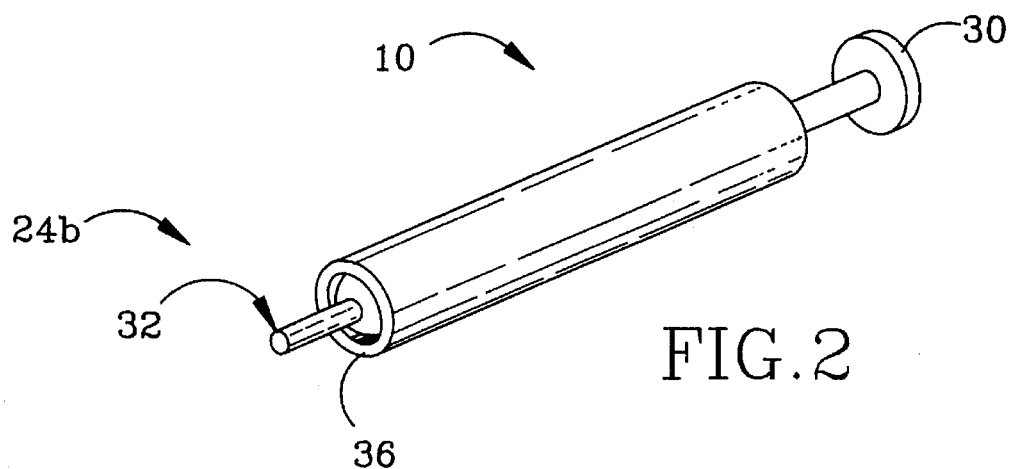
FIG. 2 is a perspective view of the syringe.

FIG. 2 is a perspective view of a conventional luer-lock type syringe 10 that can be used with the invention. A plunger 30 forces or draws fluid through a tip 32. The coupling mechanism 24b includes the tip 32 and an internally threaded annular ring 36 that is formed at the end of the syringe. The ring is formed around and spaced apart from the tip. The syringe's tip 32 is shaped for forming a pressure fit inside the hub.

Figure 3:
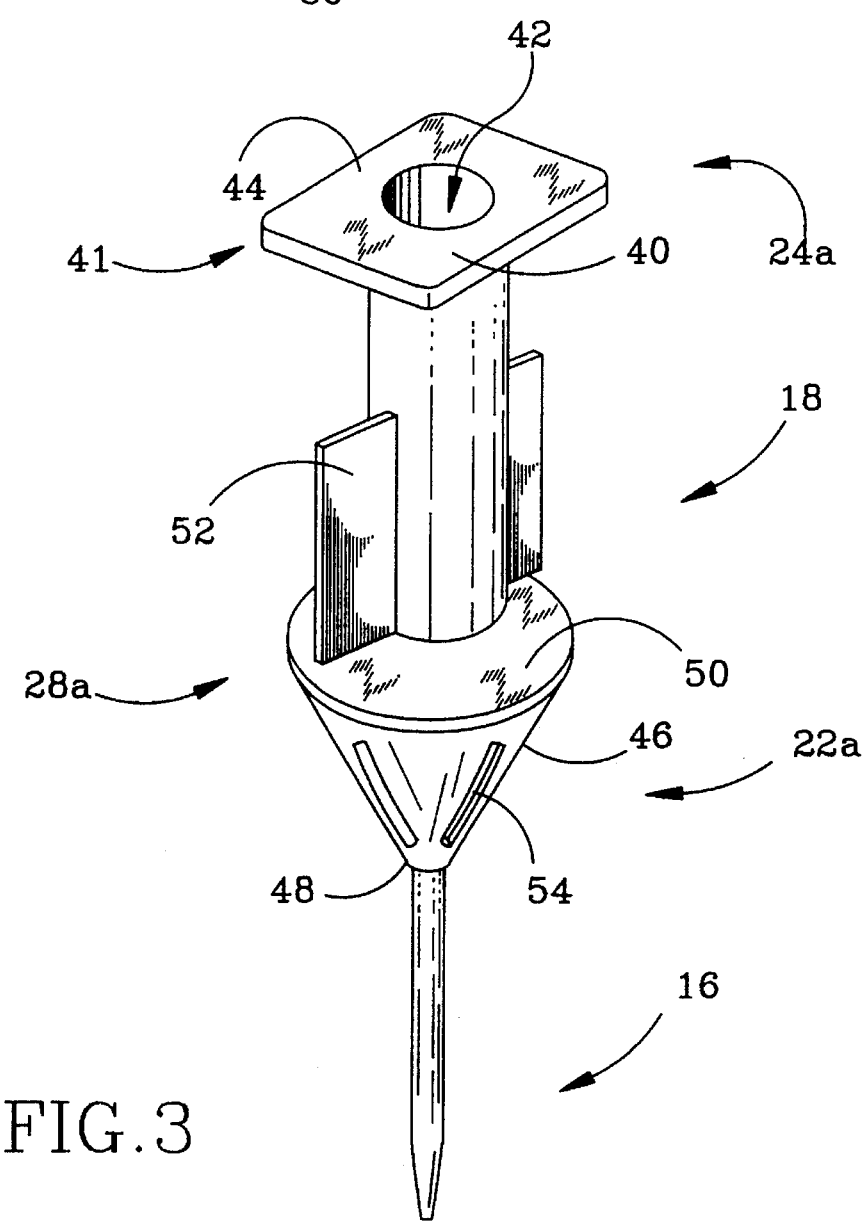
FIG. 3 is a perspective view of the hypodermic needle-hub assembly.

As shown in FIG. 3, the hub 18 preferably comprises a hollow shaft 40 that is attached to the needle 16. The opposite end 41 of the shaft is formed with an internal taper 42. The internal taper and syringe tip have complementary shapes for forming a press fit. The coupling mechanism 24a includes the internal taper 42 and a luer-lock flange 44 that is attached to end 41 of the hub. To connect the syringe to the hypodermic assembly, the syringe is threaded onto the flange 44, which presses the tip of the syringe into the hub's internal taper 42 to provide a fluid seal.

The one-way locking mechanism 28a is preferably a tapered stop 46 formed around the shaft 40 The stop's narrow end 48 faces the needle 16 and its base 50 faces the end 41 of the shaft. The locking mechanism 28a also includes a pair of wings 52 for disengaging the syringe. The wings are formed longitudinally along the shaft between the stop's base 50 and the flange 44. The temporary locking mechanism 22a comprises a pair of slots 54 that are formed in the stop 46.

Figure 4:
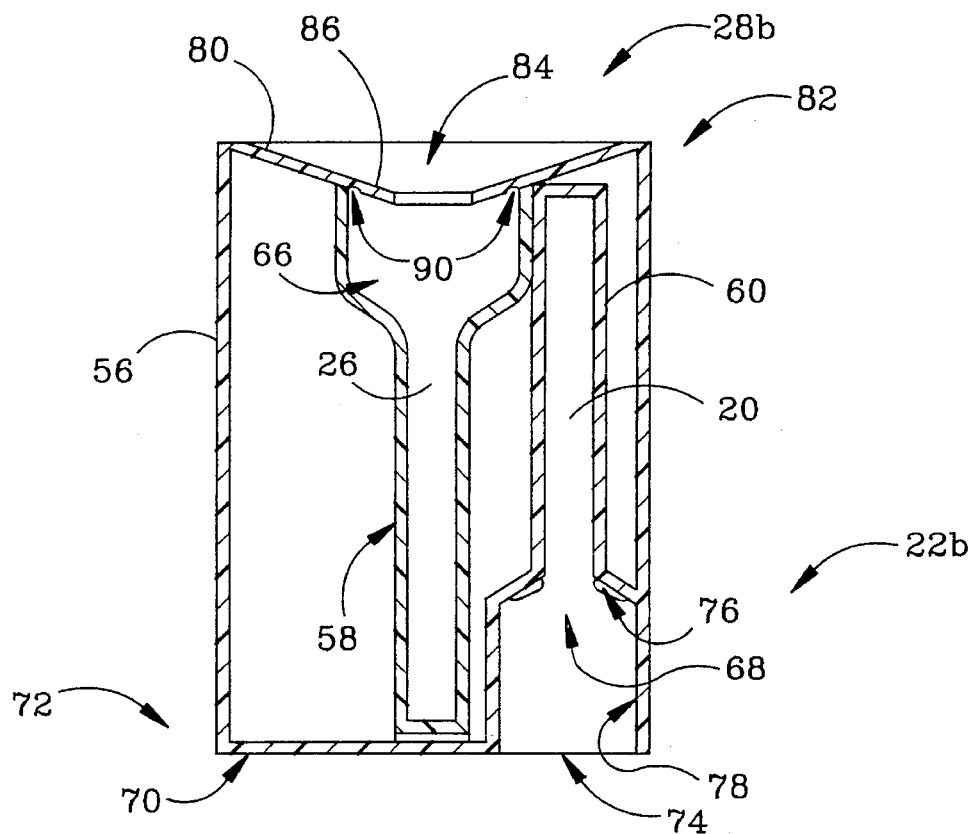
FIG. 4 is a sectional view of the safety cap.

FIG. 4 is a sectional view of the safety cap 14. The cap is preferably a molded plastic cylinder 56 that includes tubes 58 and 60 for providing the compartments 26 and 20, respectively. The tubes 58 and 60 comprise respective tapered apertures 66 and 68 for receiving the needle. The tubes and apertures are preferably formed with shapes that are complementary to the hypodermic assembly to protect the unused needle and to secure the contaminated needle. Alternatively, sleeve 58 can be removed to allow the hypodermic assembly to fall into the cylinder.

Figures 5A, 5B:
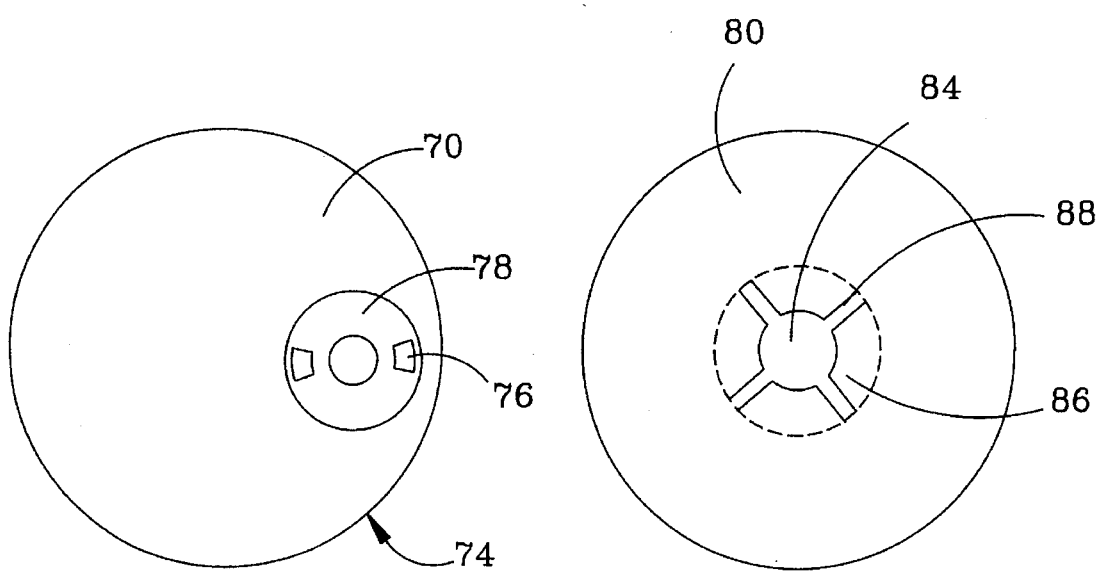
FIGS. 5a and 5b are respectively bottom and top plan views of the safety cap.

A base 70 covers the lower end 72 of the cylinder 56. The cylinder's base is preferably flat so that the cap can be stably positioned on a flat surface. To increase the base's stability, it can be coated with an adhesive to provide a tacky surface. The base allows the contaminated needle to be reinserted without having to grasp the cap. An opening 74 in base 70 is positioned over the aperture 68 of tube 60 and provides access to the tube 60 for inserting and removing the unused hypodermic assembly. The locking mechanism 22b comprises a pair of keys 76 that are formed on the interior surface 78 of the aperture 68, as shown in FIGS. 4 and 5a. The keys engage the slots 54 in the hub and prevent the hypodermic assembly from rotating, thus permitting the syringe to be attached to the hub. Other types of stands for the cap could also be used instead of the flat base 70. For example, a retractable base may be provided in which the legs come folded up against the cylinder, and then are expanded to provide a stable base. This type of base may reduce the overall size of the cap.

An annular rim 80 is attached to an upper end 82 of the cylinder 56. The cap's one-way locking mechanism 28b is preferably provided by a flexible opening 84 in the annular rim, as shown in FIGS. 4 and 5b. The rim 80 is preferably funnel shaped, which reduces its push through resistance and increases its pull back resistance. The flexible opening is positioned over aperture 66, with the tube 58 preferably being connected to the underside of rim 80.

The flexible opening 84 is preferably provided by a plurality of flexible flanges 86 that are formed along an interior edge of the annular rim. The flanges are made by forming radial slots 88 in the rim that are spaced around the opening 84 and extend outward towards the cylinder, and by forming approximately circumferential notches 90 on the underside of the rim at the base of the flanges. The slots and notches allow the flanges 86 to be deflected inward so that the opening 84 can expand, but resists bending outward. The slots 88 also serve to engage the hub wings to prevent the hub from rotating, thus allowing the syringe to be disengaged. The safety cap, tubes, annular rim and flexible flanges are preferably molded from substantially rigid plastic material. Alternatively, the annular rim could be formed from a flexible plastic or rubber material so that the opening can expand and contract without requiring flanges.

Figure 6:
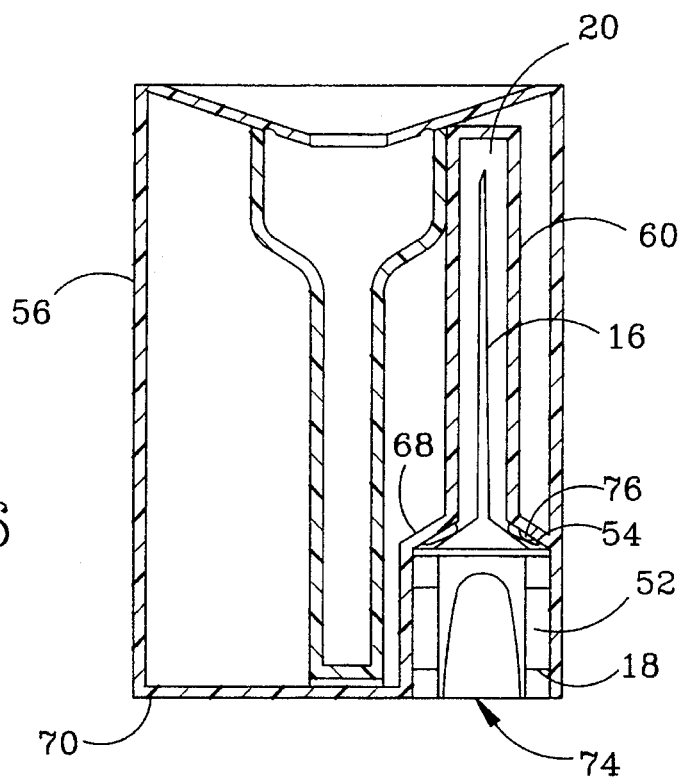
FIG. 6 is a sectional view of the unused needle-hub secured in the safety cap.

FIG. 6 is a sectional view of the safety cap 14 in which an unused hypodermic assembly 12 is stored in compartment 20. The hub 18 is secured by pressing wings 52 through the aperture 68 into tube 60 and engaging slots 54 with keys 76. The needle 16 extends into the tube 60 which protects it from physical damage and contamination.

Figure 7A:
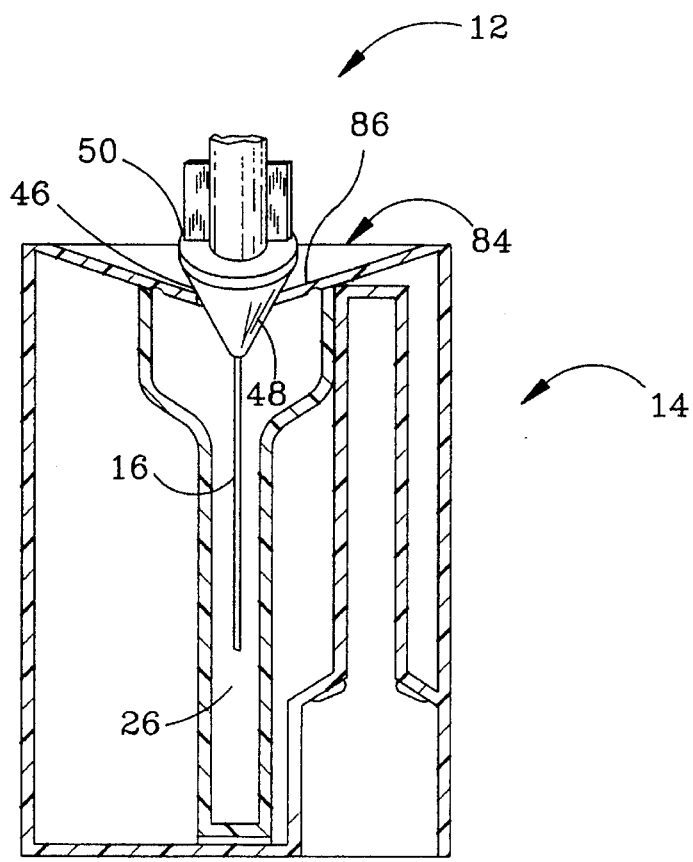
FIGS. 7a through 7c are sectional views of the safety cap showing the contaminated needle-hub being reinserted into the cap at initial, intermediate and secured positions, respectively.
Figure 7B:
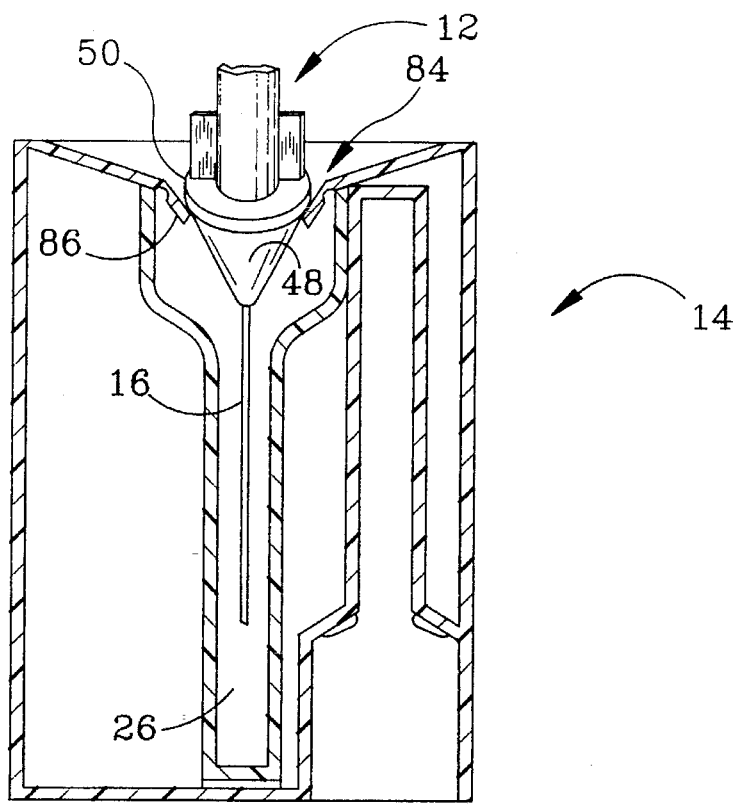
Figure 7C:
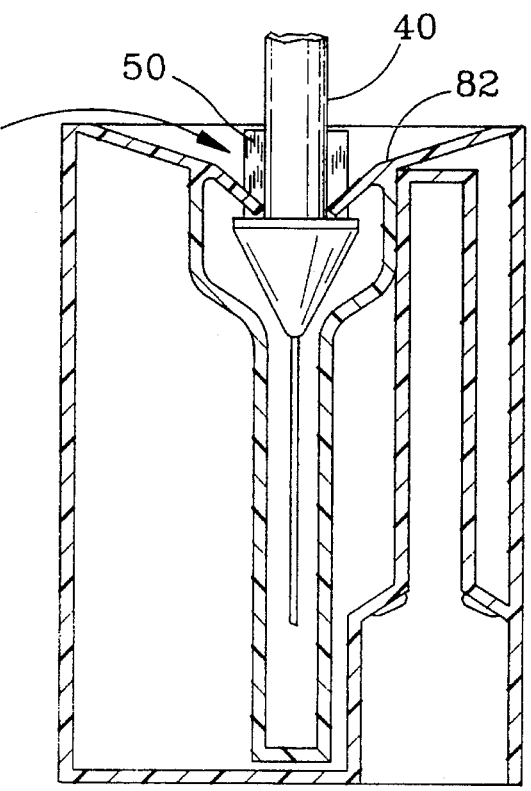

FIGS. 7a through 7c are sectional views of a used hypodermic assembly 12 being inserted into compartment 26 in the safety cap 14. In FIG. 7a the needle 16 has been inserted through the flexible opening 84 in safety cap 14 to the point where the conical hub stop 46 first contacts the flexible flanges 86. The diameter of the undeflected opening 84 is larger than the diameter of the stop's narrow end 48, but smaller than the stop's diameter at its base 50. In FIG. 7b the hypodermic assembly has been pushed further into the compartment 26 so that the flanges 86 are fully deflected, expanding the opening 84 to allow the base 50 of the hub to pass into compartment 26. In FIG. 7c the hub has been pushed all the way into the compartment 26, allowing the flanges 86 to snap back into their original position and form a fairly snug fit around the shaft 40 and wings 52. The wings fit into the slots 88 to prevent the hub from rotating. Once the contaminated needle is safely secured inside the cap, the user disengages the syringe by turning it counter-clockwise and pulling it out of the cap, and disposes of the cap and syringe.

The dimensions of the safety cap depend upon the length of the needle and the size of the syringe. For a standard 1.27 cm needle, the safety cap is suitably approximately 40 mm tall and 30 mm in diameter. The diameters at the apertures of sleeves 58 and 60 are about 11 mm and 9 mm, respectively. The diameter of opening 84 has an undeflected value of approximately 6 mm and a fully deflected value 9 mm. The complementary hub design is approximately 19 mm in length, with a maximum diameter of 9 mm at the base 50 of the stop 46 and a minimum diameter of 1.2 mm at its tip 48. The shaft 40 has a diameter of approximately 6 mm. The dimensions are selected so that the hub of the unused hypodermic assembly is press fit into sleeve 60, and the used hypodermic can be pushed through the flexible opening 84 and secured in sleeve 58. The flexible opening expands to allow the hub to pass through and then contracts to a radius (6 mm) between the radius at the tip (1.2 mm) of the hub and the radius at its base (9 mm). Once secured, the contaminated hypodermic can not be pulled back through the opening.

FIG. 8 is a sectional view of an alternative embodiment of the one-way locking mechanisms 28a and 28b for the safety cap 14 and hub 18, respectively. The flexible flanges are replaced by a plurality of flexible teeth 92 that are formed on the interior surface 94 of the sleeve 58 and point toward the bottom of the compartment 26. The flexible teeth are preferably curved, rigid plastic teeth. One end of each tooth is attached to the sleeve 58 and the other end is spaced apart from the surface so that the tooth is compressible. When the hub 18 is inserted into the sleeve 58, the stop 46 compresses the teeth against the sleeve. Once the base of the stop has passed the teeth, they spring back and lock onto the hub. Alternatively, the teeth could be mounted on the hub in the opposite direction for engaging an indented ring inside the sleeve.

FIG. 9 is a prospective view of a safety cap 96 and a scalpel 98 that comprises a handle 100 and a blade 102. The scalpel is formed with a hub 104 between the handle and blade. The unused scalpel is temporarily secured in one end of the safety cap, and the used scalpel can be pushed through the other end 106 of the cap and permanently secured inside the safety cap.

The described safety caps and complementary hub reduce the risk of accidental puncture wounds. The free-standing safety cap receives the contaminated needle or scalpel without requiring the user to hold onto the cap, and thus reduces the risk of self-puncture wounds. Once the needle or blade is reinserted, it is permanently secured inside the cap; this reduces the risk to the personnel charged with disposing of the contaminated instruments.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

I claim:

1. A safety cap comprising, a cap body with upper and lower ends and having first and second juxtaposed compartments for temporarily securing a medical instrument, which has a sharp end and a hub, before use and permanently securing it after use, respectively, said cap body having a first opening spaced from its upper end for removing said instrument from said first compartment and a second opening in the cap body's upper end for receiving said used instrument into said second compartment; and a stand at the cap body's lower end for supporting said cap in a position in which the second opening is exposed to receive the sharp end of said used instrument so that a used instrument can be inserted into the second compartment for permanent storage without grasping the cap during said insertion, said second compartment comprising a locking mechanism for engaging said hub to permanently secure the sharp end of said instrument inside said second compartment, said locking mechanism comprising a flexible annular member that is connected to said second compartment and provides said second opening so that said hub can be pushed through said second opening to secure said used instrument.

2. The safety cap of claim 1, wherein said flexible annular member flexes so that said second opening expands to allow said hub to pass through and then contracts to secure said hub.

3. The safety cap of claim 2, wherein said flexible annular member has a generally funnel shape that reduces the push through resistance and increases the pull back resistance so that the sharp end of said used instrument is permanently secured inside said second compartment.

4. The safety cap of claim 2, wherein said flexible annular member comprises a plurality of flexible flanges that are deflectable to receive and then secure said hub.

5. The safety cap of claim 4, wherein said second compartment comprises a substantially rigid annular member having an interior edge, said flexible flanges being connected to said interior edge.

6. The safety cap of claim 5, said locking mechanism further comprising a sleeve that is connected to said rigid annular member and extends inward into said second compartment to secure said hub inside said second compartment.

7. A safety cap, comprising:

a cap body with upper and lower ends and having first and second juxtaposed compartments for temporarily securing before use a medical instrument that comprises a hypodermic assembly that includes a needle and a hub, with said hypodermic assembly connected to a syringe, and permanently securing said hypodermic assembly after use, said cap body having a first opening for removing said instrument from said first compartment and a second opening in the cap body's upper end for receiving said used instrument into said second compartment, said second compartment comprising a first locking mechanism for engaging said hub to permanently secure said needle inside said second compartment, and a second locking mechanism for engaging said hub to prevent rotation of said used hypodermic assembly so that the syringe can be disengaged from said assembly; and a stand at the cap body's lower end for supporting said cap in a position in which the second opening is exposed to receive a used needle for permanent storage in said second compartment.

8. A safety cap, comprising:

a cap body having lower and upper ends, and having first and second openings formed at its lower and upper ends, respectively;

a first compartment in said cap body for temporarily securing a hypodermic assembly that includes a needle and a hub, said first compartment being accessible through said first opening to remove said hypodermic assembly;

a second compartment juxtaposed with said first compartment in said cap body for storing said hypodermic assembly;

a one-way locking mechanism that includes a flexible annular member connected at the upper end of the cap body to provide a second opening to said second compartment, said annular member responding to the insertion of the hypodermic assembly by flexing so that said second opening expands to allow said hub to pass through, and then contracting to permanently secure said hub in said second compartment; and a stand at the lower end of the cap body for supporting said cap in a position in which the second opening in the upper end of the cap body to said second compartment is exposed to receive said hypodermic assembly so that a used hypodermic assembly can be inserted into said second compartment without grasping the cap body during said insertion.

9. The safety cap of claim 8, wherein said flexible annular member comprises a plurality of flexible flanges that are deflectable to receive and then secure said hub.

10. A safety cap-hypodermic assembly for use with a syringe which has a coupling, comprising:

an unused hypodermic needle;

a hub which is attached to the needle, said hub having a complementary coupling for engaging said syringe coupling to hold the needle to the syringe, and a locking mechanism;

a cap body having upper and lower ends;

a first compartment in said cap body for temporarily securing the unused needle and hub, said first compartment having a first opening in said cap body through which said syringe can be coupled to said hub to remove said unused needle from the first compartment, said first compartment comprising a complementary locking mechanism for engaging said hub to prevent rotation of said unused hypodermic assembly so that a syringe can engage said assembly and remove it from said cap;

a second compartment in said cap body for storing said needle and hub after they have been used, said second compartment having a second opening formed in the upper end of said cap body for receiving said used needle;

a one-way locking mechanism for engaging said hub to permanently secure said used needle inside said second compartment; and a stand at the lower end of said cap body for supporting said safety cap on a flat surface in a position in which the second opening in said second compartment is exposed to receive said used needle.

11. The safety cap-hypodermic assembly of claim 10, wherein the hub's locking mechanism is a slot formed in said hub and said complementary locking mechanism is a key that is formed in said first compartment and fits into said slot.

12. A safety cap-hypodermic assembly for use with a syringe which has a coupling, comprising:

an unused hypodermic needle;

a hub which is attached to the needle, said hub having a complementary coupling for engaging said syringe coupling to hold the needle to the syringe;

a cap body having upper and lower ends;

a first compartment in said cap body for temporarily securing the unused needle and hub, said first compartment having a first opening in said cap body, spaced from its upper end, through which said syringe can be coupled to said hub to remove said unused needle from the first compartment;

a second compartment in said cap body for storing said needle and hub after they have been used, said second compartment having a second opening formed in the upper end of said cap body for receiving said used needle;

a one-way locking mechanism for engaging said hub to permanently secure said used needle inside said second compartment; and a stand at the lower end of said cap body for supporting said safety cad on a flat surface in a position in which the second opening in said second compartment is exposed to receive said used needle so that the used needle can be inserted in said second compartment without grasping the cap body during said insertion, said one-way locking mechanism comprising a flexible annular member that is connected so that said hub can be pushed through said second opening to secure said used hypodermic assembly within said second compartment.

13. The safety cap-hypodermic assembly of claim 12, wherein said hub has a tip that faces the needle and a base that faces away from the needle, and tapers from a first radius at its tip to a larger second radius at its base, said flexible annular member flexing so that said second opening expands to allow said hub to pass through and then contracting to a radius between said first and second radii to secure said hub within said second compartment.

14. A safety cap hypodermic assembly, comprising:

a syringe which has a coupling;

a hypodermic assembly which comprises an unused hypodermic needle and a hub which is attached to the needle, said hub having a complementary coupling which engages said syringe coupling to connect the hypodermic assembly to the syringe by holding the needle to the syringe;

a cap body having upper and lower ends;

a first compartment in said cap body for temporarily securing the unused needle and hub, said first compartment having a first opening in said cap body through which said syringe can be coupled to said hub to remove said unused needle from the first compartment;

a second compartment in said cap body for storing said needle and hub after they have been used, said second compartment having a second opening formed in the upper end of said cap body for receiving said used needle;

a first one-way locking mechanism for engaging said hub to permanently secure said used needle inside said second compartment; said second compartment comprising a second locking mechanism for engaging said hub to prevent rotation of said used hypodermic assembly so that the syringe can be disengaged from said assembly; and a stand at the lower end of said cap body for supporting said safety cap on a flat surface in a position in which the second opening in said second compartment is exposed to receive said used needle.

15. A method for capping a medical instrument, comprising:

providing a safety cap having upper and lower ends, said safety cap having a first compartment that secures a medical instrument which has a sharp end and a hub, a first opening to said first compartment that is spaced from the safety cap's upper end, a second compartment juxtaposed with said first compartment, a second opening in the safety cap's upper end to the second compartment, and a stand at the safety cap's lower end;

a user grasping said safety cap in one hand while withdrawing said medical instrument from said first compartment through said first opening with the user's other hand;

using said medical instrument to perform a medical procedure;

placing the safety cap's stand on a surface so that the safety cap is supported in a position at which said second opening to said second compartment is exposed to receive the sharp end of said instrument;

without grasping the safety cap, inserting said instrument's sharp end through said second opening; and permanently securing said instrument's sharp end in said second compartment.

16. The method of claim 15, wherein said medical instrument is a hypodermic assembly that includes a needle and said hub, and said instrument is withdrawn by:

attaching a syringe to said hub; and pulling said syringe to withdraw said hypodermic assembly.

17. The method of claim 16, wherein said second compartment comprises a locking mechanism complementary to said hub, and said instrument is permanently secured by:

engaging said hub with said locking mechanism to prevent rotation of said hypodermic assembly;

grasping the safety cap in one hand while turning said syringe with the other hand to disengage the syringe from said hub; and withdrawing said syringe from the safety cap.

18. The method of claim 15, wherein said safety cap includes a flexible annular member that is connected to said second compartment and provides said opening, and said instrument is inserted through said opening by pushing said hub through the opening to cause the annular member to first flex and expand said opening so that the hub can pass, and to then contract the opening to secure said instrument within said second compartment.

* * * * *